(12) United States Patent
Strittmatter et al.

(10) Patent No.: US 6,410,270 B1
(45) Date of Patent: Jun. 25, 2002

(54) **PROCESS FOR THE PREPARATION OF RECOMBINANT PROTEINS IN *E. COLI* BY HIGH CELL DENSITY FERMENTATION**

(75) Inventors: Wolfgang Strittmatter, Ober-Ramstadt; Siegfried Matzku, Zwingenberg; Dieter Riesenberg, Jena; Uwe Horn, Bad Frankenhausen; Uwe Knüpeer, Jena; Marian Kujau, Jena; Rolf Wenderoth, Jena, all of (DE); Andreas Plückthun, Zürich; Anke Krebber, Zürich, both of (CH)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/077,549

(22) PCT Filed: Nov. 28, 1996

(86) PCT No.: PCT/EP96/05260

§ 371 (c)(1),
(2), (4) Date: Nov. 16, 1998

(87) PCT Pub. No.: WO97/21829

PCT Pub. Date: Jun. 19, 1997

(30) Foreign Application Priority Data

Dec. 11, 1995 (EP) .............................................. 95119478

(51) Int. Cl.[7] ........................ C12N 15/00; C12N 15/63; C12N 1/21; C12P 21/00; C07H 21/04
(52) U.S. Cl. .................. 435/69.6; 435/69.1; 435/320.1; 435/252.33; 435/252.3; 436/548; 536/23.1; 536/23.533
(58) Field of Search .............................. 435/69.1, 320.1, 435/252.3, 252.33, 69.6, 41, 91.4, 471; 436/548; 536/23.1, 23.53

(56) References Cited

U.S. PATENT DOCUMENTS 5,558,864 A 9/1996 Bendig et al. ............ 424/133.1

FOREIGN PATENT DOCUMENTS

WO 9215683 9/1992

OTHER PUBLICATIONS

BIO/Technology, vol. 11, No. 11, Nov. 1, 1993, pp. 1271–1277, XP000608190, P. Pack, et al., "Improved bivalent miniantibodies, with identical avidity as whole antibodies, produced by high cell density fermentation of *escherichia coli*".

Journal of Biotechnology, vol. 39, No. 1, Feb. 21, 1995, pp. 59–65, XP002026053, D. Korz, et al., "Simple fed–batch technique for high cell density cultivation of *Escherichia coli*".

Journal of Biotechnology, vol. 32, No. 3, Feb. 28, 1994, pp. 289–298, XP002026054, K. Hellmuth, "Effect of growth rate on stability and gene expression of recombinant plasmids during continuous and high cell density cultivation of *Escherichia coli* TG1".

BIO/Technology, vol. 6, Dec. 1988, pp. 1402–1405, XP002026055, K. Gerdes. "The PARB (HOK/SOK) locus of plasmid R1: a general purpose plasmid stabilization system".

*Primary Examiner*—David Guzu
*Assistant Examiner*—Gerald G. Leffers, Jr.
(74) *Attorney, Agent, or Firm*—Millen, White, Zelano & Branigan, P.C.

(57) ABSTRACT

The invention relates to a fed-batch fermentation process which uses special *E. coli* host/vector systems for the purpose of efficiently forming recombinant proteins, in particular recombinant antibody molecules, preferably antibody fragments such as miniantibodies. Under the given conditions, the *E. coli* cells are able to grow at a maximum specific growth rate up to very high cell densities. After the recombinant product formation has been switched on, it is only the formed product which restricts growth; there is no growth restriction due to substrates or metabolic by-products. High space-time yields of recombinant proteins can be achieved in this manner.

30 Claims, 4 Drawing Sheets

PROCESS FOR THE PREPARATION OF RECOMBINANT PROTEINS IN *E. COLI* BY HIGH CELL DENSITY FERMENTATION

The invention relates to a fed-batch fermentation process which uses special *E. coli* host/vector systems for the efficient formation of recombinant proteins, in particular recombinant antibody molecules, in particular antibody fragments such as miniantibodies.

Under the conditions according to the invention, the *E. coli* cells can grow up to very high cell densities at a maximum specific growth rate. After recombinant formation of the product has been switched on, it is only the formed product which has a limiting effect on growth; substrates or metabolic by-products do not limit growth. In this way, and in conjunction with the novel expression vectors which are specially adapted for this purpose and which exhibit high stability, it is possible to achieve high space-time yields of recombinant proteins, which proteins exhibit high biological activity, in particular in the case of antibody fragments.

The culture of *E. coli* cells to high cell densities is an essential prerequisite for efficient recombinant protein formation. The following cultures are state of the art for this purpose: following unlimited growth ($\mu=\mu_{max}$) in the batch phase, a carbon source (glucose or glycerol) is customarily metered in, in the subsequent fed-batch phase, in a limited manner such that the formation of growth-inhibiting by-products, for example acetate, is avoided, with the consequence that the growth can be continued in a manner which is only substrate-limited ($\mu<\mu_{max}$) until high cell densities are reached (e.g. Riesenberg et al., 1991, J. Biotechnol., vol. 20, 17–28; Strandberg et al., 1994, FEMS Microbiol. Rev., vol. 14, 53–56; Korz et al., 1995, J. Biotechnol. 39, 59–65; EP-B-0 511 226). Growth at a reduced growth rate naturally results in long fermentation times and consequently also in lower space-time yields. Owing to the immediate consumption, the concentration of the carbon source in the culture solution in these fermentations is virtually zero. The substrate-limited conditions are not altered after the recombinant product formation has been switched on.

Fed-batch cultures which use *E. coli* are also known in which the carbon source is added discontinuously at relatively large time intervals and then in relatively large quantities, with a rise in the $pO_2$ value usually being used as an indicator of substrate exhaustion for the purpose of initiating the subsequent dose of the carbon source (e.g. Eppstein et al., 1989, Biotechnol. 7, 1178–1181). This procedure means frequent switching from relatively long-term substrate excess conditions to substrate limiting conditions and consequently implies metabolic imbalances.

In that which follows, fed-batch cultures are dealt with in which the cells can grow at maximum specific growth rate ($\mu=\mu max$) in the fed-batch phase. Fed-batch cultures in which relatively large quantities of carbon source are added to the culture at relatively large time intervals, in accordance with off-line determinations, for the purpose of avoiding substrate limitations are experimentally elaborate and suffer from the disadvantage that the concentration of the carbon source is constantly changing during the whole of the fermentation (e.g. Pack et al., 1993, Biotechnol., vol. 11, 1271–1277, Hahm et al., 1994, Appl. Microbiol. Biotechnol. 42, 100–107).

Fed-batch cultures have also been described in which the concentration of the carbon source is measured on-line and is regulated so that limitations are avoided, although these cultures— in particular in the high cell density region— suffer from the disadvantages which are described below. An autoclavable glucose biosensor for use of [sic] microbial fermentations in stirred tank fermenters has recently been described (M. R. Phelps et al., 1995, Biotechnol. Bioeng., vol. 46, 514–524). It was employed for *E. coli* cultures. This in-situ sensor provides, with a time delay of approximately 2 minutes, the current value in the culture solution. The signal supplied by the glucose sensor is dependent, inter alia, on the pH and $pO_2$. The sensor has not been tested in the high cell density region (X>80 g/l). It is known from experience that growths on in-situ probes when *E. coli* is used can lead to additional erroneous values at very high cell densities. In addition, it is not possible to recalibrate the sensor exactly during an ongoing fermentation. Instead of being based on measurements using an in-situ sensor, other processes are based, for example, on determining the carbon sources using on-line flow injection analysers (FIA) or on-line HPLC in a culture solution which is removed semi-continuously from the fermenter and rendered cell-free by being subjected to filtration or microcentrifugation (Kleman et al., 1991, Appl. Environ. Microbiol. 57, 910–917 and 918–923; Turner et al., 1994, Biotechnol. Bioeng. 44, 819–829). Prediction and feedback control algorithms have decreased the fluctuations in the glucose concentration during growth up to X=65 g/l (Kleman et al., 1991, Appl. Environ. Microbiol., vol. 57, 910–917). In the region of very high cell densities (from approx. 80 g/l to 150 g/l ), it becomes increasingly more difficult and more time consuming to separate the cells and the nutrient solution, so that the time delay in determining the current glucose value in the fermenter also increases in a biomass-dependent manner and makes it more difficult, or impossible, to maintain the glucose level constant. By contrast, the glucose concentration is measured with a time delay which is constant and brief using an appliance which does without this cell separation (Pfaff et al., 1995, pp. 6–11, in: Proceedings of the 6th International Conference on Computer Appl. in Biotechnol. Garmisch-Partenkirchen, FRG). According to the method of Pfaff et al., an FIA possessing an enzymic-amperometric glucose sensor is employed in the immediate vicinity of the sampling site after the culture has been diluted with a growth inhibitor.

During aerobic culture, *E. coli* cells which are not obliged by the dosage regime to grow in a sub-strate-limited manner customarily form the metabolic by-product acetate to an increased extent (Riesenberg 1991, Curr. Opinion Biotechnol., vol. 2, 380–384), which acetate accumulates in the nutrient solution and has a growth-inhibitory effect when present in relatively large quantities (Pan et al. 1987, Biotechnol. Lett., vol. 2, 89–94). For this reason, it has only previously been possible to effect fed-batch cultures to high cell densities using special *E. coli* strains whose accumulation of acetate has been reduced by means of specific genetic alterations, while tolerating other disadvantages which are associated with this. The descendants of *E. coli* K12 include phosphotransacetylase-negative mutants (Bauer et al., 1990, Appl. Environ. Microbiol., vol. 56, 1296–1302; Hahm et al., 1994, Appl. Microbiol. Biotechnol., vol. 42, 100–107) whose growth is, however, strongly reduced in glucose/mineral salt media. Phelps and collaborators (see above) used the *E. coli* strain TOPP5 as the host for non-substrate-limited culture up to a biomass of X=85 g/l. However, this *E. coli* strain, which evidently does not accumulate acetate in a pronounced manner, is not a K12 strain. *E. coli* TOPP5 forms haemolysin and is consequently a pathogenic strain which is not suitable, for reasons of safety, for use as a host for forming recombinant DNA products in the industrial sector. A reduction in acetate accumulation by means of specifically reorienting the intermediary metabolism was achieved by transforming E. coli cells with a plasmid containing a gene encoding acetolactate synthase (ALS) (San et al., 1994, in: Ann.N.Y.Acad.Sci., vol. 721, 257–267). However, this procedure suffers from the disadvantage that instabilities usually occur under high cell density conditions when an ALS-encoding plasmid is used in combination with a second plasmid carrying the "production" gene. The efficiency of recombinant product formations is frequently decreased by plasmid instabilities, which occur to an increased extent particularly in association with culture to very high cell densities.

Antibodies or antibody fragments, such as Fab', F(ab')2, miniantibodies or single-chain Fv's, are gaining ever increasing importance in the medical and biotechnological spheres. In that which follows, a miniantibody is to be understood, according to the invention, to be a bivalent or bispecific single-chain Fv fragment which is linked by way of a pseudohinge region. In this context, it can be important, for example in cancer therapy, to make available large quantities of antibodies (approximately 1 g/dose). In this respect, monovalent antibody fragments or fusion proteins of these fragments, or multimeric or multispecific variants thereof, can be particularly readily and satisfactorily prepared in E. coli . These fragments or variants are of a small size which is associated with a high specific binding capacity. (E.g. Plückthun A., 1992, Immunol. Rev. 130, 151–188; Pack et al., 1995, J. Mol. Biol. 246, 28–34.) However, proteins and antibodies, in particular, must be correctly folded in order to be biologically and functionally active. When considering the yield of formed antibody fragment per cell, attention must be paid to this problem in connection with the cell density. Furthermore, the primary sequence of the antibody is of importance in determining the yield in vitro and the folding in vivo (Knappik A. and Plückthun A., 1995, Protein Engin. 8, 81–89). Thus, Fab fragments, for example, are expressed as insoluble cytoplasmic or periplasmic aggregates and refolded in vitro. Thus, yields of about 0.14 g/l at low cell density (Condra et al., 1990, J. Biol. Chem. 265, 2292–2295) and of up to about 1-2 g/l of insoluble antibodies at medium cell density (Shibui et al., 1993, Appl. Microbiol. Biotechnol. 38, 770–775) have been reported. Bivalent miniantibodies (Pack et al., 1993, Biotechnol. 11, 1993, 1271–1277) can also be obtained in E. coli in biologically functional form in yields of about 0.2 g/l. On average, approximately 5–45% of these yields is properly refolded.

In the known E. coli systems, the formation of foreign protein is, as a rule, switched on in a suitable manner, after appropriate cell densities have been reached, by a regulatable promoter system corresponding to the expression system. Examples of promoter systems which may be mentioned here are (i) the araBAD promoter in the presence of the AraC repressor (inducible by arabinose) (e.g. Better et al., 1993, Proc. Natl. Acad. Sci. (USA) 90, 457–461), (ii) the phoA promoter (inducible by withdrawing phosphate) (e.g. Carter et al., 1992, Biotechnol. 10, 163–167) and (iii) the lac promoter system (inducible by IPTG) (Pack et al., 1993, loc. cit.) . While the lac system brings about good expression as a rule, it suffers from the disadvantage that, on the one hand, undesirable basal expression is observed prior to induction of the promoter and, on the other, plasmid instability is observed following induction with ITPG [sic].

In a particular embodiment of the invention, a special vector (pHKK) is described which contains, as the foreign gene, sequences which encode fragments of the murine or humanized antibody Mab 425. Mab 425 (ATCC HB 9629) is a murine monoclonal antibody which was isolated from the known human A432 cancer cell line (ATCC CRL 1555) and binds to the epitope of human epidermal growth factor receptor (EGFR, a glycoprotein of about 170 kD) while inhibiting the binding of the natural ligand EGF. It has been demonstrated that Mab 425 has a cytotoxic effect on tumour cells or is able to impair the growth of these cells (Rodeck et al., Cancer Res. 1987, 47: 3692). WO 92/15683 discloses humanized and chimeric forms of Mab 425, including the DNA and amino acid sequences of their light and heavy chains.

The object of the invention was to make available a process for preparing foreign proteins, in particular antibody fragments, in recombinant E. coli cells under high cell density conditions (HCDC=high cell density culture) with high space-time yields, and without any substantial impairment of growth by substrates or metabolites and without significant plasmid losses or plasmid instabilities, while ensuring that the expressed protein exhibits a high degree of effective biological activity (binding capacity and correct folding).

The process according to the invention is a multi-step batch process which is primarily notable for the fact that the cells are able to grow at a maximum rate during the whole of the batch ($\mu=\mu_{max}$). Thus, cell densities of from 100 to 150 g/l (bio dry mass [sic]) can ultimately be achieved using the described process. Furthermore, the growth is not inhibited to an important extent by acetate accumulation since, surprisingly, such an accumulation is not particularly pronounced under the conditions which are selected, in particular when E. coli strains are used which in any case only tend to form decreased quantities of acetate during the fermentation. This is achieved by, also in association with a series of other additional measures, first and foremost, in the fed-batch phase which is inserted after a batch phase, keeping the concentration of the carbon source in the medium constant in a defined range while maintaining unlimited growth of the cells. By designing the relevant expression vector in an appropriate manner, the undesirable basal expression of protein, prior to switching on protein synthesis by means of a regulatable promoter system, can also be virtually eliminated, as can the plasmid loss, which is sometimes substantial and which, as already mentioned above, can normally be observed in expression systems using strong promoters such as the lac promoter system.

Protein yields of on average from 3 to 5 g/l can be achieved after a total culture time of from approx. 25 to 35 hours. In the case of the antibody fragments, in particular miniantibodies, which are particularly critical owing to their folding criteria, approximately 80% of the synthesized material is biologically active and correctly folded.

The invention consequently relates to a process for preparing foreign protein, in E. coli cells which have been transformed with a plasmid carrying the foreign gene and an inducible promoter, by means of high cell density fermentation by way of batch and fed-batch stages, without any restriction of growth by sub-strates or metabolic by-products, and isolation and purification of the expressed protein from the culture medium, with the concentration of substrates in the fed-batch phase being controlled using a continuous, automated or semi-automated analysis and addition system, with, in the fed-batch phase, (i) the concentration of the carbon source in the medium being kept constant in a range between 0.1 g/l and 25 g/l while maintaining unlimited growth of the cells ($\mu=\mu_{max}$), (ii) the production of the foreign protein being started in the said fed-batch phase by inducing the promoter at a cell density of between 10 and 80 g/l, and (iii) utilizable nitrogen and phosphate, and also salts of trace elements, being fed in continuously after induction of product synthesis has taken place, where (iv) the $pO_2$ value is adjusted to between 5 and 25% during the whole of the fed-batch phase by passing oxygen into the fermentation broth in an appropriate manner.

The values according to the invention for the requisite concentration of the carbon source during the fed-batch phase are in a range from 0.1 g to 25 g/l. A preferred range is between 0.5 and 15 g/l, in particular from 1.0 to 5 g/l, or from 1.0 to 3 g/l. The particularly preferred concentration is 1.5 g/l. Preferred carbon sources which may be mentioned are glucose or glycerol or mixtures of these two compounds. According to the invention, the carbon source is added in a continuous manner (on-line) using an automated or semi-automated addition and analysis system. An on-line flow injection analysis system (FIA) is preferably employed.

The feeding-in of utilizable nitrogen, preferably ammonium nitrogen and phosphate, for example diammonium hydrogen phosphate or ammonium dihydrogen phosphate, and also trace elements, for example salts of boron, manganese, copper, molybdenum, cobalt, iron or zinc which are soluble in the medium, takes place in the fed-batch phase which is inserted after the batch phase, preferably after switching on protein synthesis using the regulatable promoter, at a cell density of from 50 to 80 g/l (bio dry mass [sic]), preferably at about 70 g/l, at a total growth rate [sic] of 100 to 150, preferably 140, g/l.

According to the invention, protein synthesis is switched on, by activating the regulatable promoter system, at a cell density of from 10 to 80 g/l, preferably from 20 to 60 g/l; very particularly preferably, the range is from 40 to 50 g/l.

During the fed-batch phase, the partial pressure of oxygen is between 5 and 25%, preferably between 15 and 25%, very particularly preferably 20%.

According to the invention, the pH of the fermentation medium has to be adjusted, during the whole batch, to between 6.5 and 7.0, preferably to between 6.7 and 6.9, in particular to 6.8.

The invention furthermore relates to a corresponding process in which an expression vector is employed which possesses an expression cassette which contained [sic] the foreign gene and is flanked by two terminator sequences. These terminator sequences, in particular that which is positioned upstream, successfully prevent unwanted expression of protein prior to the expression being switched on by the promoter system. While the terminator thp (Nohno et al., 1988, J. Bacteriol. 170, 4097–4102) is particularly suitable, other known terminator sequences may also be employed.

The invention furthermore relates to a process in which the expression vector which is employed additionally contains a suicide system. The suicide system produces a protein which is toxic for the cell if the plasmid is not present in the cell. Suitable suicide systems are known from the literature. A suicide system which is particularly suitable for the invention is the hok-sok system (e.g. Gerdes K., 1988, Biotechnol. 6, 1402–1405). Thus, it is important, for the process for effectively forming recombinant proteins, in particular antibody molecules, that the host/vector system is characterized, in the high cell density region, by high plasmid stability, low recombinant basal expression and high product formation. In this context, suicide systems, in combination with recombinant expression cassettes which are flanked by terminators, are vector-specific.

The invention furthermore relates to a corresponding process in which a foreign gene is employed which encodes an antibody fragment, in particular a miniantibody.

The invention also relates to a process in which expression vectors are employed which possess additional features which are described below.

In principle, most of the *E. coli* strains can be employed which are known and which are suitable for recombination technology and for production on an industrial scale. Advantageously, those strains are preferably used which accumulate relatively little acetate during growth to high cell densities. Those strains are particularly suitable which exhibit an acetate enrichment of less than 5 g/l. Surprisingly, the acetate accumulation can be kept particularly low by using the chosen conditions of the process according to the invention. The well known and commercially available *E. coli* strain RV308 (ACCC [sic] 31608), and its variants having the same effect, is particularly suitable in this regard.

The invention therefore relates, in particular, to a corresponding process in which an *E. coli* strain is employed which exhibits an acetate accumulation of less than 5 g/l in the culture medium during the fermentation.

The invention also relates to an *E. coli* expression vector which is suitable for expressing foreign proteins under high cell density fermentation conditions and which exhibits the following features:

| | |
|---|---|
| (i) | an upstream terminator sequence and a downstream terminator sequence, |
| (ii) | the lac promoter/operator system, |
| (iii) | a T7g10 Shine Delgarno sequence, |
| (iv) | the pelB or ompA signal sequence, |
| (v) | the sequence of the foreign gene, | and, in a preferred embodiment, also a suicide system, in particular the hok-sok suicide system.

According to the invention, the promoter system can also be replaced by other suitable systems, for example those mentioned above. Likewise, other signal sequences and control sequences having the same effect are also encompassed by the invention.

Finally, the invention relates to the expression vector pHKK (FIG. 2), which is defined by its construction and which contains the sequences for the miniantibody which is derived from Mab 425, and to a special recombinant *E. coli* host RV308[pHKK], as special embodiments.

Figure 1:
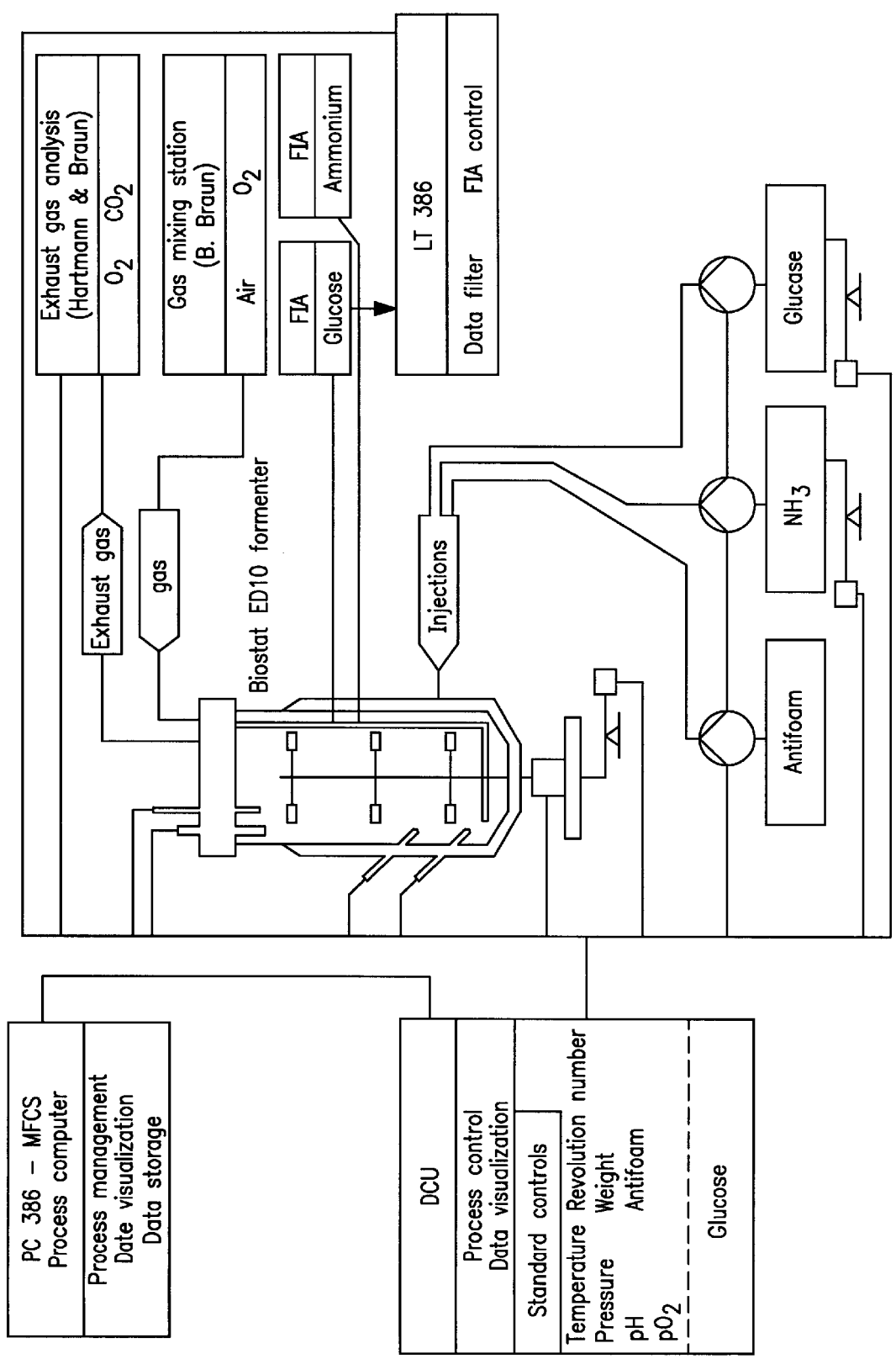
FIG. 1: Experimental set-up of the bioreactor for preparing proteins under high cell density conditions. The system is equipped with a measuring device, a display device, a control device and a metering device.

The process according to the invention uses transformed *E. coli* host cells. The plasmid constructs which are chosen depend on the nature of the protein which is to be expressed. Features of those plasmid constructs which are particularly favourable are described below. The techniques and methods which are required for plasmid construction and for host cell transformation are all known and described in detail in the literature (e.g. Sambrook et al., 1989, Molecular Cloning: A Laboratory Manual, Cold Spring Harbor). In addition, they are explained in the examples using the particular embodiments of the invention. Starting plasmids or plasmid parts are either obtainable commercially or can be constructed without difficulty using standard methods which are based on known construction schemes.

The preceding batch phase of a typical fermentation, according to the invention, of transformed *E. coli* cells is divided into two subphases. Following inoculation with an appropriate preliminary culture, subphase I is characterized by a lag phase in which the cells adapt and the growth rate $\mu$ subsequently rises to $\mu_{max}$. During subphase II, the cells grow exponentially at $\mu=\mu_{max}$. After the $pO_2$ has dropped from 100% saturation down to less than 5–15%, the $pO_2$ value is adjusted, by controlling the speed of the $pO_2$ agitator, to $pO_2$ values which are preferably between 15 and 25%, preferably around 20% (FIG. 3c). This adjustment (by passing in air which is enriched with pure oxygen) should be performed at about 6 to 12 hours after beginning fermentation of the main culture. The glucose concentration, which was preferably initially between 20 and 35 g/l, declines to the end of subphase II, which also constitutes the end of the batch phase preceding the fed-batch phase. In this connection, the glucose concentration values should under no circumstances fall below 0.1 g/l. From now on, this is prevented by the appropriate feeding-in of glucose (subphase III, FIG. 3a, start of the fed-batch phase). In accordance with the invention, the glucose value is kept constant between 0.1 and 25 g/l, preferably, however, between 1 and 3 g/l. The feed medium FS1 (Tab. 1) can, for example, be used for this purpose. Since this glucose concentration range is sufficiently far above the $K_s$ value for glucose (Bergter, 1983, "Wachstum von Mikroorganismen (Growth of microorganisms)", p. 41, Gustav Fischer Verlag, Jena), the cells can continue to grow at $\mu_{max}$. According to the invention, the glucose concentration is monitored and regulated using an automated or semi-automated system. Flow injection analyser systems in on-line operation are particularly suitable. Purely manual or largely manual systems have been found to be inappropriate. While the fed-batch phase begins between about hours 15 and 22, this ultimately depends on various individual factors such as temperature, medium composition, medium concentration, reactor size, etc., and in particular also on the nature of the *E. coli* strain employed. Advantageously, synthesis of the foreign protein is switched on at about from 4 to 8 hours after beginning the fed-batch phase. However, the precise time depends ultimately on the cell density of the culture which has already been reached at this time. Cell densities of between 10 and 80 g/l, preferably between 20 and 60 g/l, are particularly favourable if final cell densities of from 100 to 150 g/l can be reached. It is consequently generally favourable for starting the protein synthesis if from about 10 to 60% of the maximum cell density to be reached is present at the time of induction.

Protein synthesis is brought about by switching on the regulatable promoter system. Depending on the system which is used, this switching-on is as a rule effected by adding a substance or by altering a physical quantity. In the case of the preferred lac system (promoter, operator and inducer) the switching-on is effected by adding IPTG (isopropyl thiogalactopyranoside). The further growth of the cells is now only restricted by the accumulating product. For this reason, it is important, according to the invention, that no significant basal expression, which would exert an unfavourable influence on total growth and consequently on total yield, can take place prior to induction. According to the invention, this is contrived by the expression cassette in the plasmid being flanked by efficient terminator sequences.

Figure 3A:
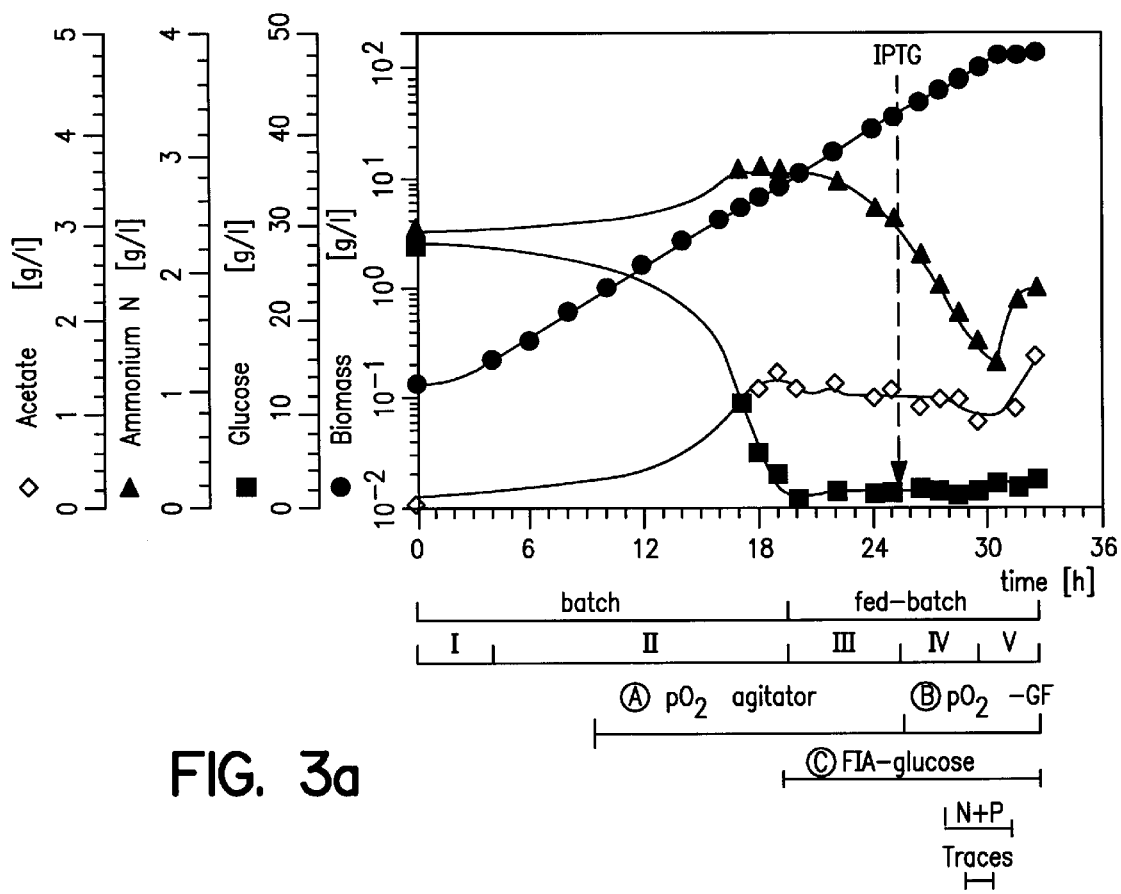
FIG. 3(Panels A-D): HCD culture of recombinant *E. coli* using the example of *E. coli* RV308[pHKK]: chronological course of biomass, glucose, ammonium nitrogen, phosphate, acetate, stirrer speed, $PO_2$, $O_2$ and $CO_2$ in the exhaust gas, plasmid stability (expressed as % of β-lactamase-positive colonies) and formation of protein (in this case: scFv$_{425}$dhlx). The batch and fed-batch phases are divided into 5 sub-phases. The IPTG arrow indicates the start of protein production.
Figure 3B:
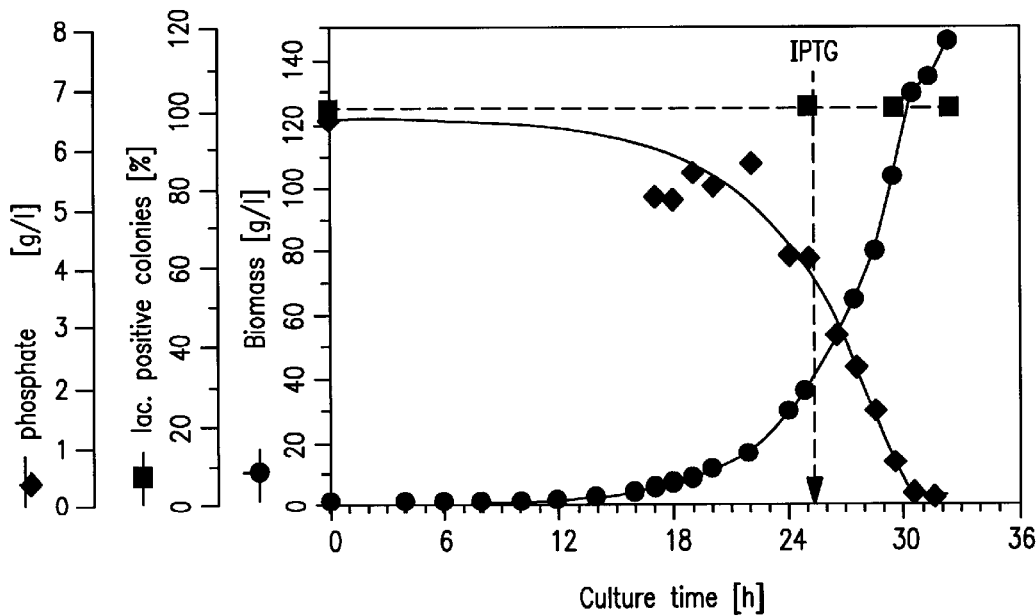
Figure 3C:
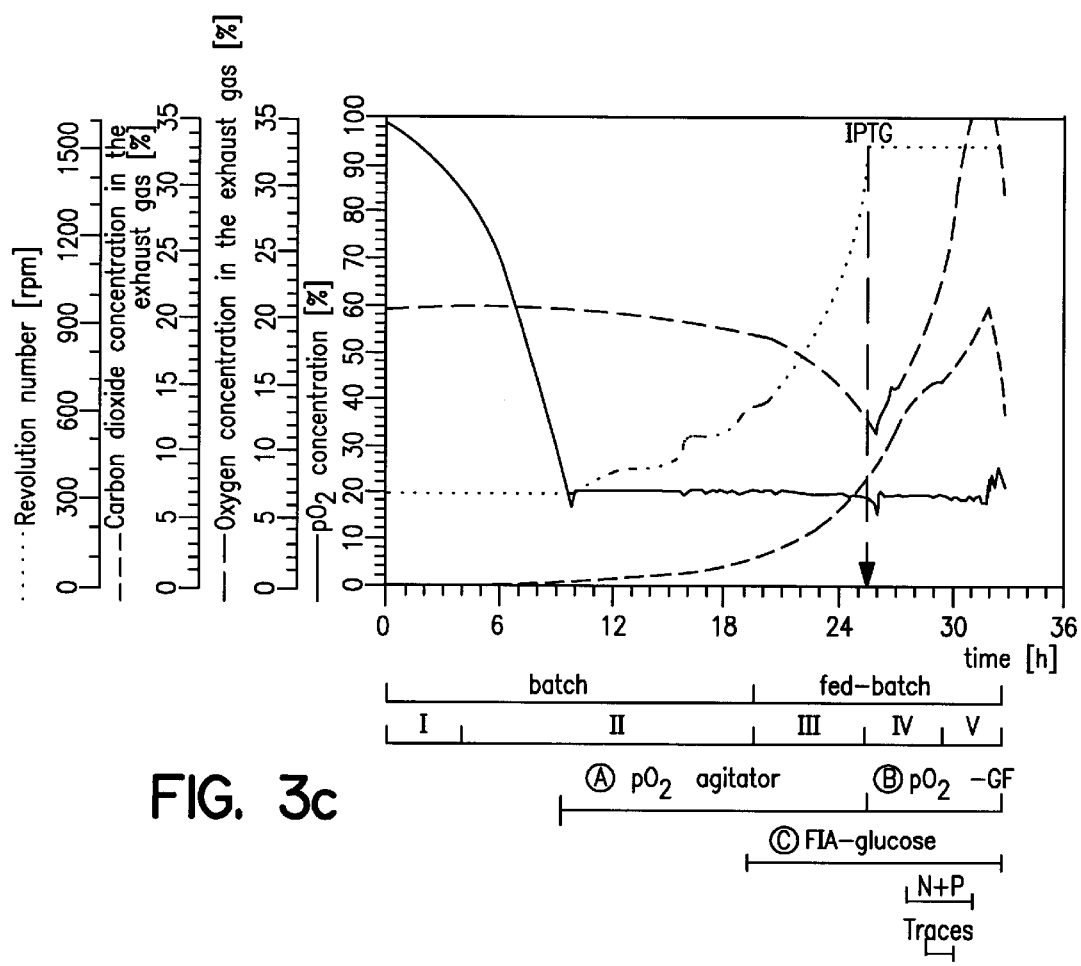
Figure 3D:
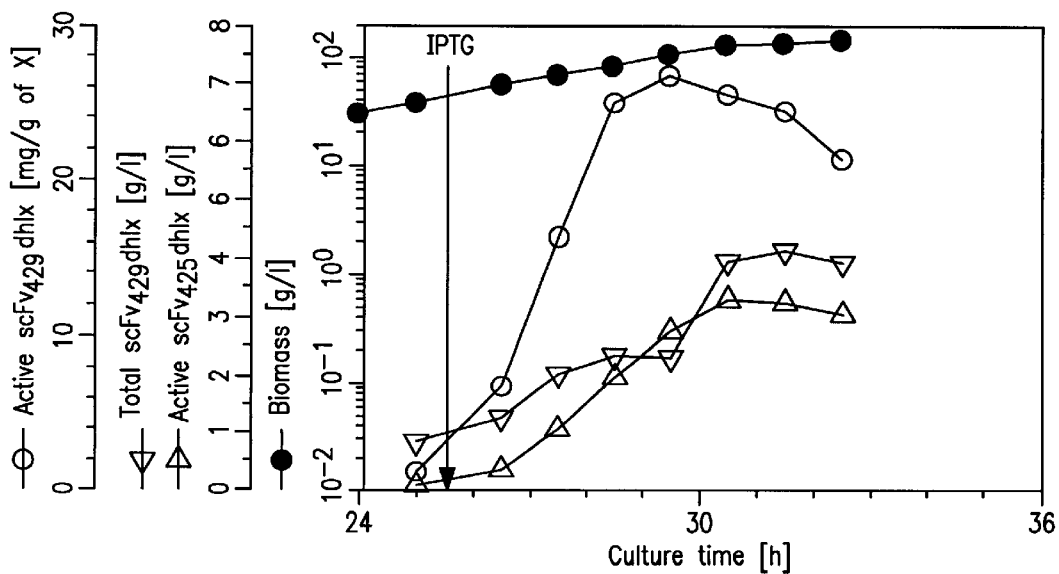

From the time at which glucose begins to be fed in, the fermentation medium becomes impoverished in nitrogen and phosphate (FIGS. 3a, b). In order to avoid limitations of any nature, nitrogen and phosphate are preferably likewise fed in by means of an appropriate continuous process. Expediently nitrogen is supplied in the form of ammonium salts since, in this way, influence can also simultaneously be brought to bear on the pH (from 6.5 to 7.0, preferably 6.8). For example, the solution FS2 is suitable (Tab. 1). Subphase IV is characterized by the supply, according to the invention, of trace elements (e.g. boron, manganese, iron, cobalt, molybdenum and Zn) in the form of their soluble salts. As a rule, the addition is effected continuously at a constant rate. Subphase V is characterized by reduced growth, primarily due to product accumulation. In addition, a slight increase in the acetate concentration can be observed. However, the accumulation of acetate, and the concentration of acetate, in the medium are surprisingly low. This is also to be attributed to the special process conditions. *E. coli* strains which exhibit a maximal acetate enrichment during the fermentation of <5 g/l markedly strengthen this effect still further.

Depending on the nature of the protein, the yields of protein vary on average between 2 and 6 g/l. Of this, between 50 and 95% is biologically active, again depending on the nature of the protein. In the case of antibody fragments, more than 80% of the protein which is obtained is refolded. These values markedly exceed those obtained in comparable processes which have previously been described in the state of the art.

Preference is given to using the process which has been described, including the expression plasmids which have been specially constructed and adapted for this purpose, for efficiently preparing antibody fragments, in particular miniantibodies. However, it is also possible advantageously to prepare many other proteins, fusion proteins or enzymes using the process according to the invention. Examples of such suitable proteins are hybrid streptokinase and glucose dehydrogenase, or else proteins which have an effect on blood coagulation, for example hirudin, thrombin, hementin or theromin.

TABLE 1

Composition of the media; FS1, FS2 and FS3 constitute the feed media which are used in the different subphases of the fed-batch phase

| | Compound | Preliminary culture medium mg/l | Main culture medium mg/l | FS1 mg/l | FS2 mg/l | FS3 mg/l |
|---|---|---|---|---|---|---|
| 1 | $Na_2HPO_4 \times 2H_2O$ | $8.6 \times 10^3$ | | | | |
| 2 | $K_2HPO_4$ | $3 \times 10^3$ | $16.6 \times 10^3$ | | | |
| 3 | $(NH_4)_2HPO_4$ | | $4 \times 10^3$ | | $227 \times 10^3$ | |
| 4 | $(NH_4)H_2PO_4$ | | | | | $169.5 \times 10^3$ |

TABLE 1-continued

Composition of the media; FS1, FS2 and FS3 constitute the feed media which are used in the different subphases of the fed-batch phase

| | Compound | Preliminary culture medium mg/l | Main culture medium mg/l | FS1 mg/l | FS2 mg/l | FS3 mg/l |
|---|---|---|---|---|---|---|
| 5 | $NH_4Cl$ | $1 \times 10^3$ | | | | |
| 6 | NaCl | $5 \times 10^2$ | | | | |
| 7 | Citric acid | | $2.1 \times 10^3$ | | | |
| 8 | Fe(III) citrate hydrate | 60.0 | 75.0 | | | $5 \times 10^3$ |
| 9 | $H_3BO_3$ | 3.0 | 3.8 | | | 250 |
| 10 | $MnCl_2 \times 4H_2O$ | 15.0 | 18.8 | | | 125 |
| 11 | $EDTA \times 2H_2O$ | 8.4 | 10.5 | | | 700 |
| 12 | $CuCl_2 \times 2H_2O$ | 1.5 | 1.9 | | | 125 |
| 13 | $Na_2MO_4 \times 2H_2O$ | 2.5 | 3.1 | | | 213 |
| 14 | $CoCl_2 \times 6H_2O$ | 2.5 | 3.1 | | | 213 |
| 15 | $Zn(CH_3COO)_2 \times 2H_2O$ | 8.0 | 10 | | | 668 |
| 16 | Glucose | $10 \times 10^3$ | $25 \times 10^3$ | $670 \times 10^3$ | | |
| 17 | $MgSO_4 \times 7H_2O$ | 600 | $1.5 \times 10^3$ | $19.8 \times 10^3$ | | |
| 18 | Ampicillin | 100 | 100 | | | |

EXAMPLE 1

The prototrophic *E. coli* K12 strain RV308 (lac74-galISII::OP308strA) (Maurer et al., 1980, J. Mol. Biol. 139, 147–161; ATCC 31608) was used to prepare a recombinant *E. coli* host. Unless explained elsewhere, transformation with a vector which was suitable for the expression, and all other requisite DNA manipulations, were effected using standard methods. Plasmid-free *E. coli* RV308 cells were employed as the control in a corresponding high cell density fermentation.

Figure 2:
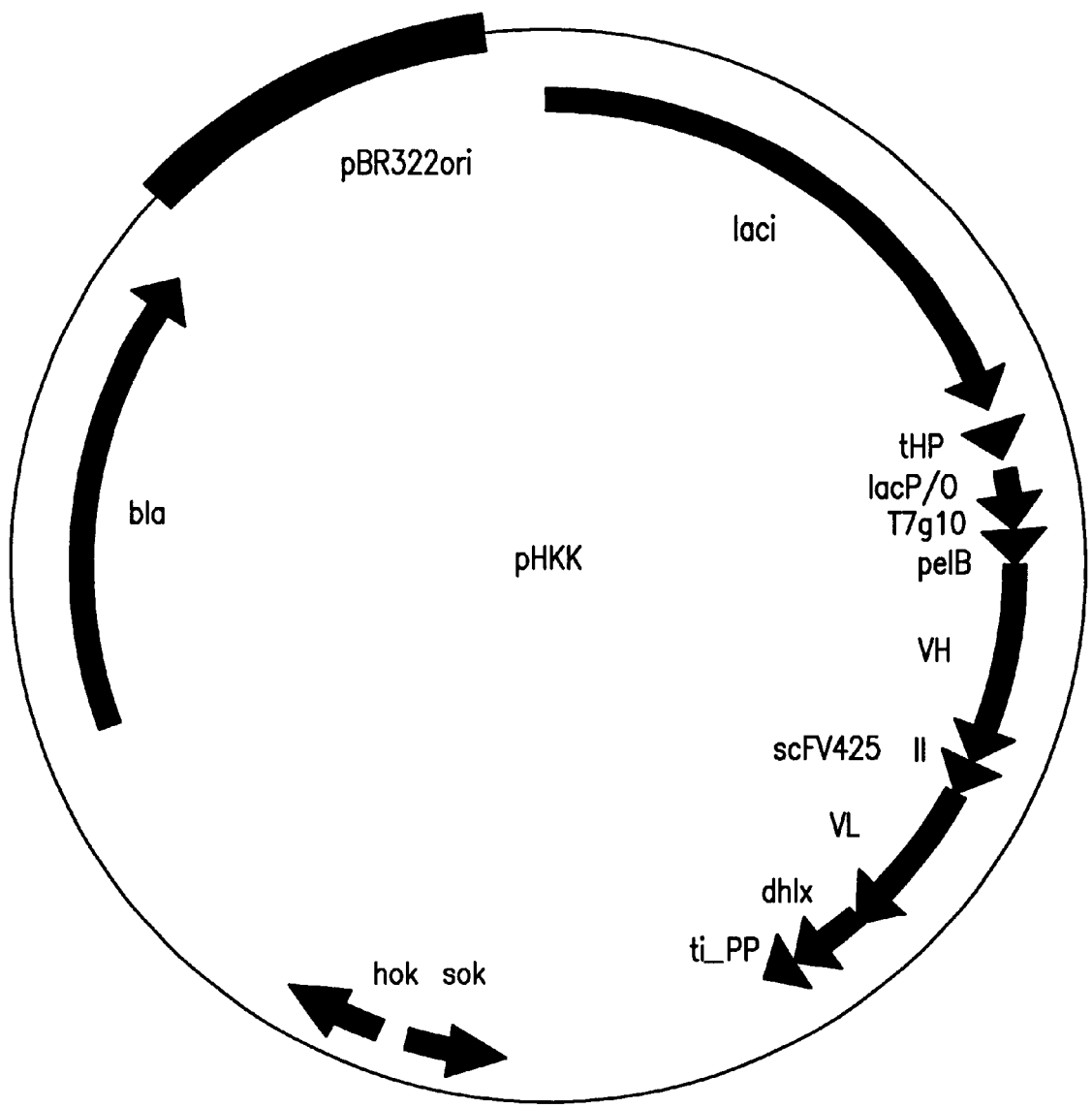
FIG. 2: Optimized expression vector PHKK and constituent parts of its construction. The vector is essentially made up of constituent parts from the known vectors pASK40, pAK100 and pKG1022.

The vector pHKK was constructed as follows (FIG. 2): the small MluI fragment from pAK100 (Krebber and Plückthun, 1995), which contains the strong transcriptional terminator tHp (Nono et al., see above) in the upstream region of lac p/o, was inserted into the plasmid pASK40 (Skerra et al., 1991, Biotechnol. 9, 273–278). The hok-sok DNA was inserted by means of two further cloning steps: the aphA gene from pKG1022 (Gerdes, 1988, see above) was removed by double digestion with XhoI and EcoRI, filled in with DNA polymerase I (Klenow fragment) and religated. In a second step, the modified BamHI fragment from pKG1022 was cloned into the single BamHI cleavage site of the first cloning product. The miniantibody is derived from a single-chain ab fragment in which the variable domains in the $V_H$-$V_L$ direction were connected to a flexible linker (gly$_4$ser)$_3$, followed by a proline-rich hinge region and a modified helix-turn-helix domain (dhlx) (Pack et al., 1993, Biotechnol. 11, 1271–1277). The DNA sequences, primers, amplifications and clonings of the light and heavy chain of murine/humanized Mab 425 are described in detail in WO 92/15683. In order to ensure secretion of the scFv425dhlx fragment into the periplasm, the $V_H$ domain was fused N-terminally to the pelB signal sequence. The T7g10 ribosomal binding site (Shine Dalgarno) was cloned, using PCR methodology, into the XbaI and SfiI cleavage sites of pEGl (Strittmatter et al., 1995). The finally finished scFv425dhlx expression cassette was cloned between the XhaI and HindIII cleavage sites. This gave the expression vector PHKK which is depicted in FIG. 2.

EXAMPLE 2

The compositions of the media for the preliminary cultures in Erlenmeyer flasks, of the main culture in a tank reactor equipped with an agitator mechanism (Biostat ED10, B. Braun, Biotech International, Melsungen, FRG), and of the feed media FS1, FS2 and FS3, are compiled in Table 1. The main culture medium (8 l) was modified as compared with the medium of Riesenberg et al., 1991 (see above). In order to prevent precipitations, the constituents were added in the sequence given in Tab. 1. Glucose and magnesium sulphate were added as separately autoclaved solutions. The reactor was operated at 26° C., a pressure of 0.15 MPa, a pH of 6.8 and an average aeration rate of 10 1/min. 25% aqueous ammonia was used to adjust the pH. Ammonia and Ucolub N115®(Fragol Industrieschmierstoffe GmbH, Müihleim/Ruhr, FRG) were added during the fermentation, by means of sensor control, in order to regulate the pH and as a defoaming agent, respectively. FS1 was prepared as follows: 750 g of glucose and 22.2 g of $MgSO_{4x}7H_2O$ were dissolved separately in 600 ml of $H_2O$ and 50 ml of $H_2O$, respectively. The solutions were mixed with each other after having been autoclaved. FS2 was prepared by dissolving 227 g of $(NH_4)_2HPO_4$ and 169.5 g of $(NH_4)H_2PO_4$ in water while at the same time adding 60 ml of 25% $NH_3$ in order to adjust the pH to 6.8 prior to autoclaving. FS3 was prepared from stock solutions in the following sequence: 50 ml of Fe(III) citrate hydrate (6 g/l), 0.5 ml of $H_3BO_3$ (30 g/l), 0.5 ml of $MnCl_2 \times 4H_2O$ (10 g/l), 0.5 ml of $EDTA \times 2H_2O$ (84 g/l), 0.5 ml of $CuCl_2 \times 2H_2O$ (15 g/l), 0.5 ml of $Na_2MoO_4 \times 2H_2O$ (25 g/l), 0.5 ml of $CoCl_2 \times 2H_2O$ (25 g/l) and 10 ml of $Zn(CH_3COO)_2 \times 2H_2O$ (4 g/l).

EXAMPLE 3

Several colonies from a Petri dish, where they had been grown on LB agar at 26° C., were used to overinoculate 20 ml of liquid LB medium. After 5 hours of shaking (200 rpm, 26° C.), 1 ml was transferred to 100 ml of preliminary culture medium in a 500 ml flask and the latter was then subjected to further incubation. 10 ml of this preliminary culture were used in order to overinoculate 100 ml of new preliminary culture medium. In this way, 9 preliminary cultures were produced which were used together to overinoculate 8 l of main culture medium in the fermenter to an initial $OD_{550} \approx 0.2$.

EXAMPLE 4

The set-up of the 10 l bioreactor, together with accessories and control equipment, is depicted in FIG. 1. The culture on a high cell density fermentation scale was effected using a digital measuring and control unit (DCU), a multifermenter control system (MFCS) and a gas flow control unit. $CO_2$ and oxygen release were measured constantly. Following overinoculation, the biosample collector MX-3 (New Brunswick Scientific, Watford, UK) was used for taking aseptic samples and permitting off-line data analysis (Webb et al., 1990, Biotechnol. 8, 926–928). The control units maintained an admission gas flow rate of 10 l/min, a pH of 6.8, a temperature of 26° C. and a pressure of 0.15 MPa. Two control loops guaranteed aerobic growth conditions at a $pO_2$ of 20%. All the important physical quantities were displayed and recorded during the whole of the fermentation.

During the fed-batch phase, the glucose concentration in the culture is maintained at 1.5 g/l. A modified flow injection analyser (FIAstar 5020 analyser equipped with a photometer and a detection control unit, Tecator AB, Sweden) was used for this purpose. Details of this system, and of its mode of operation, are described in the state of the art (e.g. Pfaff et al., 1995, in Munack A. and Schügerl K (eds): Computer Applications in Biotechnology, Elesvier [sic] Science Ltd., Oxford, 6–11).

The cell density was calculated by measuring the optical density at 550 nm. The plasmid stability was determined by the method of Pack et al., 1993 (see above).

EXAMPLE 5

The synthesized miniantibodies were determined quantitatively using the method of Pack et al., 1993 (see above). The quantity of functional miniantibodies was determined by ELISA and the total quantity of miniantibodies by SDS-PAGE in an 12% polyacrylamide gel, in accordance with Laemmli (1970), followed by gel-scanning. For the ELISAs, microtitre plates were coated with human EGFR receptor (e.g. from WO 92/15683). The bound miniantibodies were detected with anti-scFv425 rabbit serum and peroxidase-conjugated goat anti-rabbit IgG (Jackson Immunoresearch Inc., USA). The yield of active miniantibodies was calculated from dilution series prepared from the purified miniantibodies. In a control, it was demonstrated that the anti-scFv425 rabbit serum did not exhibit any observable cross reaction with other components of the plasmid-free crude extract of E. coli RV308. Furthermore, addition of this crude extract to a dilution series prepared from the same antibody in purified form had no effect on the ELISA signals. In order to determine the total quantity of miniantibodies, gels stained with Coomassie brilliant blue were detected photometrically and the concentration of the miniantibodies was calculated from a dilution series prepared from the purified miniantibody which had been fractionated on the same gel. An analogous mixture in which E. coli host cells were used which did not produce any miniantibodies served as the control.

We claim:

1. A high density fermentation process for producing a foreign protein from E. coli cells which have been transforrned with a plasmid carrying an inducible promoter and, regulated by that promoter, a nucleic acid which encodes the protein, wherein there is no restriction of cell growth by substrates or metabolic by-products, comprising
    a) culturing the cells under batch fermentation conditions, then
    b) performing a fed-batch step, wherein the concentration of the carbon source in the medium is kept in a range from 0.1 g/l to 25 g/l while maintaining unlimited growth of the cells, and the $pO_2$ is adjusted to between 5 and 25% by passing oxygen into the fermentation broth, which comprises
        i) inducing the promoter at a cell density of between 10 and 80 g/l, thereby initiating the production of the foreign protein, and then
        ii) continuously feeding in utilizable nitrogen, phosphate, and salts of trace elements.

2. The process according to claim 1, wherein the concentration of carbon source is kept at 1 to 3 g/l during the fed-batch step.

3. The process according claim 1, wherein niotrogen, phosphate and trace elements are added at a cell density of 50 to 80 g/l.

4. The process according claim 1, wherein the promoter is induced at a cell density of 20 to 60 .

5. The process according to claim 1, wherein a cell density of 100 to 150 g/l is achieved in the fed-batch step.

6. The process according to claim 1, wherein the nucleic acid which encodes the foreign protein is in an expression cassette and is flanked at each end by a transcriptional terminator sequence.

7. The process according claim 6, wherein the expression vector further comprises a suicide system.

8. The process according to claim 7, wherein the suicide system is the hok-sok suicide system.

9. The process according claim 6, wherein the nucleic acid encodes an antibody fragment.

10. The process according to claim 9, wherein the antibody fragment is a miniantibody.

11. The process according to claim 1, wherein the nucleic acid which encodes the foreign protein is an expression vector which further comprises
    (i) an upstream terminator sequence and a downstream transcriptional terminator sequence, which flank the nucleic acid,
    (ii) the lac promoter/operator system,
    (iii) a T7g10 Shine Dalgarno sequence, and
    (iv) the pelB or ompA signal sequence.

12. The process according to claim 1, wherein during the fermentation phase, not more than 5 g/l acetate accumulates in the culture medium.

13. The proces according to claim 12, wherein the E. Coli cells are strain RV308.

14. The process according to claim 1, wherein the batch-fed step is controlled by using a continuous, automated or semi-automated analysis and addition system.

15. The process according to claim 1, further comprising isolating and purifying the protein from the culture medium.

16. The process according to claim 1, wherein the concentration of the carbon source in the fed-batch step is 1.5 g/l.

17. The process according to claim 1, wherein the carbon source is glucose, glycerol or a mixture of glucose and glycerol.

18. The process according to claim 1, wherein the utilizable nitrogen is ammonium nitrogen.

19. The process according to claim 1, wherein the promoter is induced at a cell density of 40 to 50g/l.

20. The process according to claim 1, wherein the pO2 is adjusted to 20%.

21. The process according to claim 1, further comprising maintaining the pH of the fermentation medium at 6.5 to 7.0.

22. The process according to claim 21, wherein the pH is maintained at 6.8.

23. An *E. coli* expression vector, suitable for expressing a foreign protein under high cell density fermentation conditions, comprising
(i) a ucleic acid encoding the foreign protein,
(ii) an upstream terminator sequence and a downstream transcriptional terminator sequence, which flank the nucleic acid,
(iii) the lac promoter/operator system,
(iv) a T7g 10 Shine Delgarno sequence, and
(v) the pelB or ompA signal sequence.

24. The vector according claim 23, which further comprises a suicide system.

25. The vector according to claim 23, wherein the upstream terminator sequence is $t_{HP}$ and the downstream terminator sequence is $t_{LPP}$.

26. The vector according to claim 23, wherein the nucleic acid encodes the $V_H$ chain and the $V_L$ chain of a miniantibody.

27. The expression vector having the designation pHKK according to the construction scheme depicted in FIG. 2.

28. The vector according to claim 24, wherein the suicide system is the hok-sok suicide system.

29. A transformed *E. coli* expression host, obtained by transforming RV308 with an expression vector according to claim 23.

30. A transformed *E. coli* expression host RV308(pHKK), obtained by transforming RV308 with an expression vector according claim 27.

* * * * *

UNITED STATES PATENT AND TRADEMARK OFFICE
CERTIFICATE OF CORRECTION

PATENT NO. : 6,410,270 B1
DATED : June 25, 2002
INVENTOR(S) : Wolfgang Strittmatter It is certified that error appears in the above-identified patent and that said Letters Patent is hereby corrected as shown below:

Column 11,
Line 57, reads "transforrned" should read -- transformed --

Column 12,
Line 9, reads "of carbon" should read -- of the carbon -- and "Delgarno" should read -- Dalgarno --
Line 11, reads "niotrogen" should read -- nitrogen --
Line 15, reads "20 to 60" should read -- 20 to 60 g/l --
Line 41, reads "in during" should read -- in, during --
Line 61, reads "50g/l" should read -- 50 g/l --
Line 62, reads "pO2" should read -- $p_o2$ --

Column 13,
Line 4, reads "ucleic" should read -- nucleic --

Signed and Sealed this

Twenty-fifth Day of January, 2005

JON W. DUDAS
*Director of the United States Patent and Trademark Office*